United States Patent [19]

Lyons

[11] Patent Number: 5,023,954
[45] Date of Patent: Jun. 18, 1991

[54] FOREHEAD, TEMPLE, EAR, AND NECK PROTECTOR

[76] Inventor: Calvin R. Lyons, 7 Worthington Ct., Sterling, Va. 22170

[21] Appl. No.: 451,561

[22] Filed: Dec. 18, 1989

[51] Int. Cl.⁵ .............................................. A42B 1/16
[52] U.S. Cl. .......................................... 2/174; 2/209
[58] Field of Search .......................... 2/174, 209, 198; 132/212

[56] References Cited

U.S. PATENT DOCUMENTS

| | | | |
|---|---|---|---|
| 2,136,039 | 11/1938 | Clancy | 2/174 |
| 2,424,352 | 7/1947 | Conjurske | 2/174 |
| 2,446,122 | 7/1948 | Bills | 2/174 |
| 2,593,892 | 4/1952 | Kindel | 2/174 X |
| 2,729,823 | 1/1956 | Foster | 2/174 |
| 3,235,882 | 2/1966 | Coleman | 2/174 |
| 4,133,052 | 1/1979 | Hodgman et al. | 2/174 |

Primary Examiner—Peter Nerbun
Attorney, Agent, or Firm—Nies, Kurz, Bergert & Tamburro

[57] ABSTRACT

A forehead, temple, ear, and neck protector (11) to simultaneously protect the skin areas of the forehead, temples, ears, and neck from the irritation or burn that can be caused by overexposure to the high temperatures of heat generated by heat based hair styling devices such as curling irons, waving irons, hot combs, blow dryers, and the like. This device is constructed of a single piece of flexible material, includes detachable ear protectors which can withstand momentary contact with heated hair styling devices and is also durable enough to withstand the laundering process. The protector (11) includes a forehead protector (12) that extends from the edge of the hairline to the lower portion of the forehead, just above the eyebrows to completely cover and protect the forehead. The forehead protector (12) extends to a left side temple protector (14) and a right side temple protector (16) on the left and right side temples, respectively. The temple protectors extend from the edge of the hairline in the area of the forehead down the left and right sides and covers the ear protectors (22) to hold them securely in place. The ear protectors (22) fit over each ear for protection. The temple protectors extend to the left neck (18) and right neck protectors (20) and fasten together to complete a closed loop configuration around the wearer's head.

19 Claims, 2 Drawing Sheets

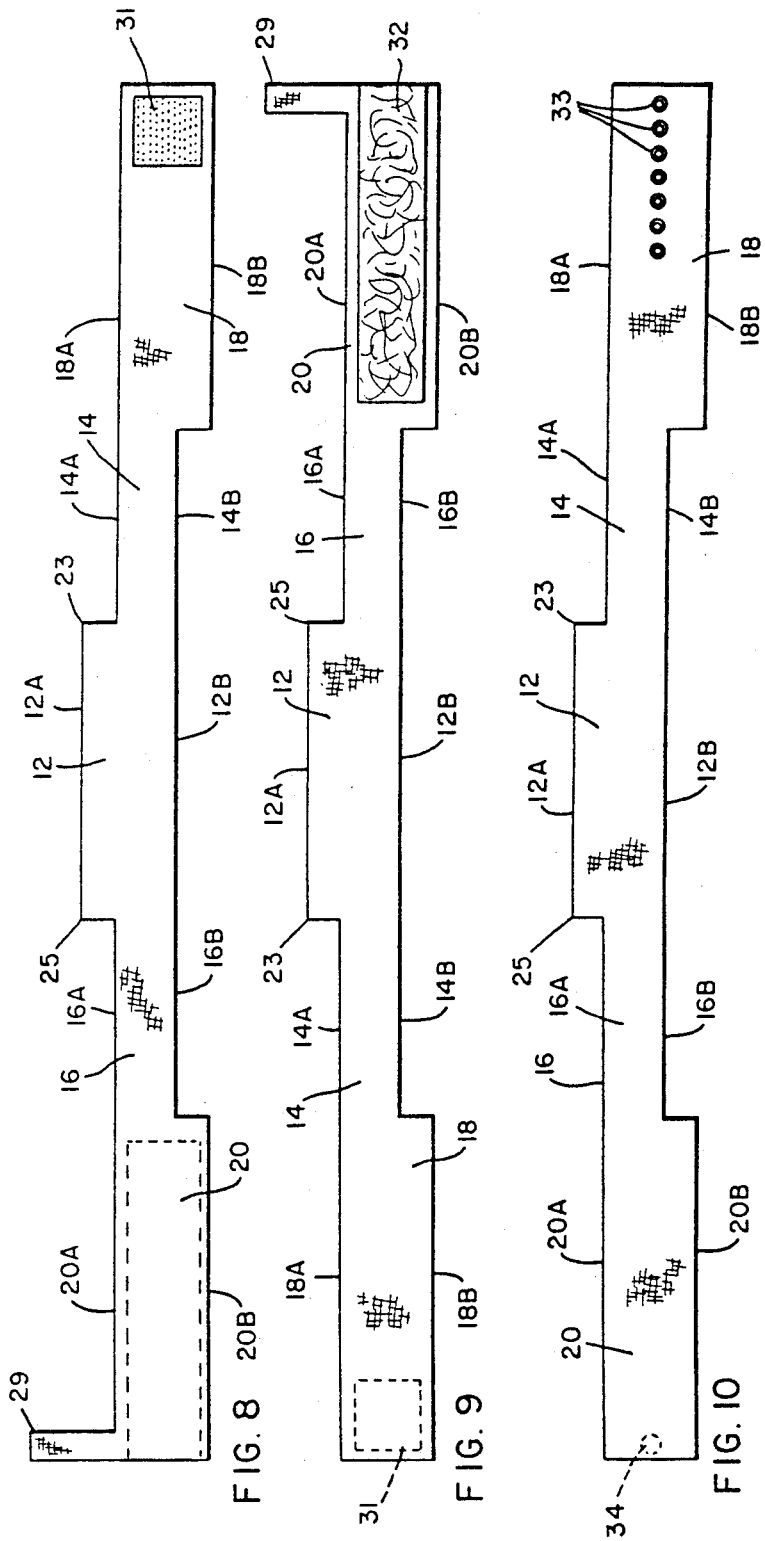
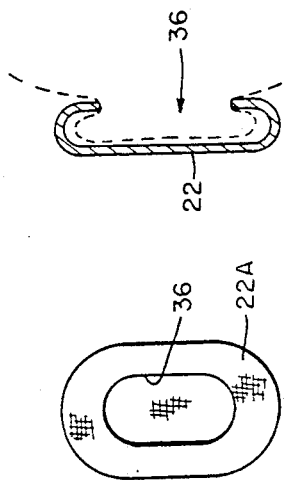
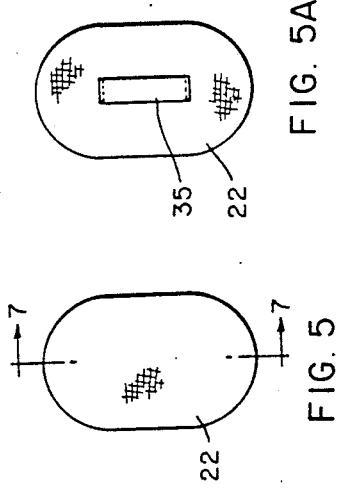

FOREHEAD, TEMPLE, EAR, AND NECK PROTECTOR

BACKGROUND

1. Field of Invention

This invention relates in general to a skin protective device, and in particular to a skin protective device for the forehead, temples, ears, and neck, designed for use with heat producing hair care devices such as those used to curl, wave, or dry the hair.

2. Description of Prior Art

Since the use of heat based hair styling devices such as the curling iron and hot comb became popular, the human skin has suffered from the irritation, discomfort, burning and discoloration that overexposure to heat can cause. This is not only annoying and unsightly, but in some incidents long term or extensive permanent damage may be experienced.

After years of observing burn marks on the foreheads, temples, ears, and necks of my loved ones, friends, and colleagues which were caused by heat based hair appliances, it was decided that an investigation into the reasons why so many ladies did not use protection to prevent accidental burning was warranted. Surprisingly, it was discovered that none of the victims knew of any product to prevent these accidental burns which sometimes left permanent scars. After days of searching for existing patents, I finally located two patents which may be considered prior art. After determining neither of these patents satisfied the needs of thousands of potential burn victims, I proceeded with my idea. This specification and drawings represents my efforts.

Inventors have created two devices, an Ear and Neck Protector and an Ear and Forehead Protector, which are designed for use with heat based hair appliances. U.S. Pat. No. 2,149,210 to Fairchild (1939) discloses a device for ear and neck protection during a beauty salon procedure. However, this device protects only the ears and neck of the wearer from the hot air currents produced by mechanical hair dryers. The Fairchild design does not protect areas of the skin such as the forehead or temples, which are frequently burned while using several types of heat based hair styling devices such as the curling iron or hot comb.

U.S. Pat. No. 2,159,435 to Gribbin (1939) discloses a device for protection of the ears and forehead. No consideration has been given specifically to the neck area which represents an area of the skin that is frequently burned while using several types of heat based hair styling devices such as the curling iron or hot comb. The Gribbin ear and forehead protector lacks adjustability. It is formed from a single piece of material which is not adjustable and therefore inconveniently requires the selection of the appropriate size before use.

The existing skin protectors do not provide the skin protection required during normal use of some heat based hair styling appliances. All vulnerable skin areas are not covered simultaneously by either of these existing designs. The vulnerable skin areas are directly below the entire hairline, including the ears. Additionally, the designs do not possess the adjustability to conform to all head sizes, while simultaneously protecting all of the vulnerable skin areas. Lastly, the existing designs do not provide separate detachable ear protectors which allow for more efficient use and protection.

Whatever the precise merits, features and advantages of the above cited references, neither of them achieves or fulfills the purposes of the forehead, temple, ear and neck protector of the present invention.

Existing known protectors designed for use with machines utilizing heat for the styling of hair heretofore known suffer from a number of disadvantages:

(a) They have not been designed to protect all potentially affected areas of the skin, specifically the forehead, temples, ears, and neck, simultaneously b) The designs lack the adjustability to cover all vulnerable skin areas without interfering with the hair styling process (c) The existing protectors are not adjustable as necessary to conform to all head sizes, while simultaneously protecting all vulnerable skin areas (d) Designs do not offer the added versatility of detachable ear protectors

OBJECTS AND ADVANTAGES

Accordingly, several objects and advantages of the present invention are:

(a) to provide a simple and efficient device for the protection of the forehead, temples, ears, and neck skin areas simultaneously from damage caused by overexposure to the heat of certain appliances such as those used for curling or drying hair;

(b) to provide a skin protection device that can h=quickly and easily attached and detached by the wearer;

(c) to provide a device designed specifically to cover all vulnerable skin areas located under the entire hairline without interfering with the hair styling process;

(d) to provide a device constructed with adjustable fasteners which allow for conformance to all head sizes with minimal effort;

(e) to provide a skin protector that protects the ears utilizing ear protectors that are detachable from the temple protector portion, providing added versatility;

(f) to provide a device constructed of a material that can protect the skin from overexposure incurred during normal use of heat based hair styling appliances;

(g) to provide a device constructed of a durable, flexible material which can be readily laundered and kept in sanitary condition;

(h) to provide a device that can be constructed from a variety of materials possessing the characteristics stated above and provide a finished product of various colors and/or patterns; Further objects and advantages of my invention will become apparent from consideration of the drawings and ensuing descriptions.

SUMMARY, RAMIFICATIONS, AND SCOPE

This present invention is a forehead, temple, ear and neck protector that can be efficiently used to protect the vulnerable skin areas of the forehead, temples, ears and neck simultaneously from the irritation, pain, burn, and discoloration that may be experienced when using heat based hair styling appliances. Applicant is unaware of any device which provides the necessary protection to all vulnerable areas simultaneously.

This design comprises an adjustable band which covers and extends over the forehead, ears, left and right temples, and neck and fastens at the rear of the neck and is capable of shielding the skin from the high temperatures of heat produced by normal use of heat based hair styling devices. Furthermore, the forehead, temple, ear and neck protector has additional advantages in that it provides a compact device that quickly and easily attaches to the head of the wearer and follows the natural contour of the hairline;

it provides the necessary protection to the vulnerable skin areas without obstructing the hair styling process;

it provides a skin protecting device that conforms to all head sizes with minimal effort and provides a tuck to hold the excess overlapped material securely into place;

it provides protection for the ear areas that can be used as detached protectors or may be attached to the temple protector portion of the device;

it provides a skin protector fabricated from a material that can be readily laundered and kept in a sanitary condition;

it provides a device that can be constructed from a variety of materials and the finished product can be of various colors and/or patterns;

Although the above description contains many specificities, these should not be construed as limiting the scope of the invention but as merely providing illustrations of some of the presently preferred embodiments of this invention. For example, the closure may be made of other fastener types such as a zipper or a hook and eye. The ear protectors may also be attached to the temple protector portion by various means such as Velcro(TM) or hook and loop type fasteners.

Thus the scope of the invention should be determined by the appended claims and their legal equivalents, rather than by the examples given.

DRAWING FIGURES

The present invention comprises certain novel constructions, combinations, and arrangement of parts as illustrated in the accompanying drawings and more particularly pointed out in the appended claims.

In the drawings, closely related figures have the same number but different alphabetic suffixes.

FIG. 5 shows the front view of a detached ear protector. FIG. 5A shows a second embodiment of the ear protector with a loop for attachment to a temple protector portion of the protector.

FIG. 6 shows the rear view of the protector.

FIG. 7 shows the section view of line 7—7 of FIG. 5.

FIG. 8 shows the front view of the head protector, shown in FIGS. 1 through 4, when laid flat.

FIG. 9 shows the rear view of the head protector shown in FIG. 8.

FIG. 10 shows the front view of another embodiment of a head protector, in accordance with the present invention, when laid flat.

REFERENCE NUMERALS IN DRAWINGS

| 11 | Forehead, Temple, Ear, and Neck Protector |
|---|---|
| 12 | Forehead Protector |
| 12A | Top Edge of Forehead Protector |
| 12B | Bottom Edge of Forehead Protector |
| 14 | Left Temple Protector |
| 14A | Top Edge of Left Temple Protector |
| 14B | Bottom Edge of Left Temple Protector |
| 16 | Right Temple Protector |
| 16A | Top Edge of Right Temple Protector |
| 16B | Bottom Edge of Right Temple Protector |
| 18 | Left Neck Protector |
| 18A | Top Edge of Left Neck Protector |
| 18B | Bottom Edge of Right Neck Protector |
| 20 | Right Neck Protector |
| 20A | Top Edge of Right Neck Protector |
| 20B | Bottom Edge of Right Neck Protector |
| 22 | Front Ear Protector Portion |
| 22A | Rear Ear Protector Portion |
| 23 | Left Forehead/Temple Offset |
| 25 | Right Forehead/Temple Offset |
| 29 | Tab |
| 30 | Tab in Fastened Position |
| 31 | Velcro TM Fastening Element |
| 32 | Velcro TM Fastening Element |
| 33 | Female Snaps |
| 34 | Male Snaps |
| 35 | Ear Protector Attachment Loop |
| 36 | Ear Protector Opening |

DESCRIPTION - FIGS. 1 TO 10

Figure 1:
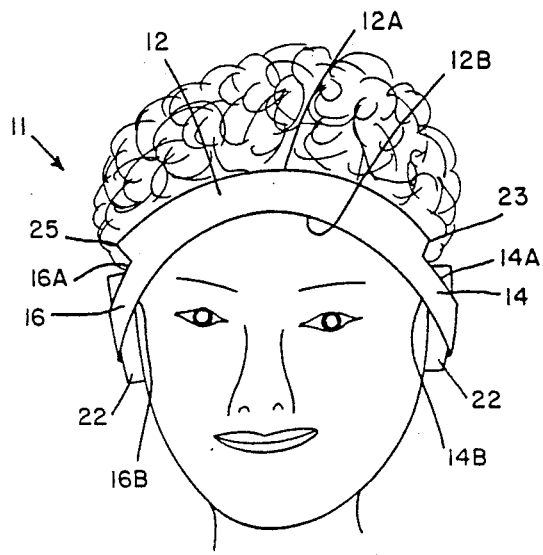
FIG. 1 is a front view showing a forehead, temple, ear, and neck protector on the wearer's head in accordance with the present invention.
Figure 2:
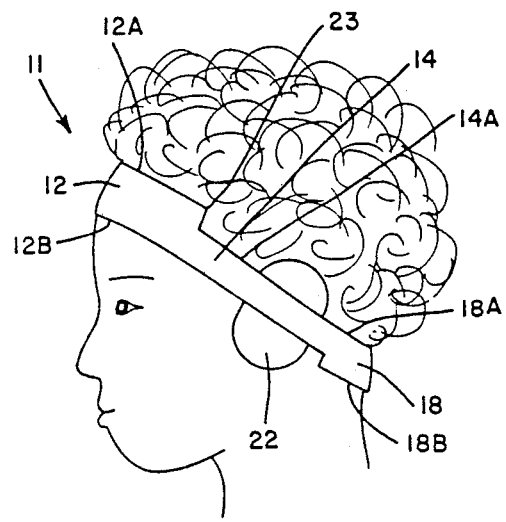
FIG. 2 is a left side view showing the protector on the wearer's head in accordance with the present invention.
Figure 3:
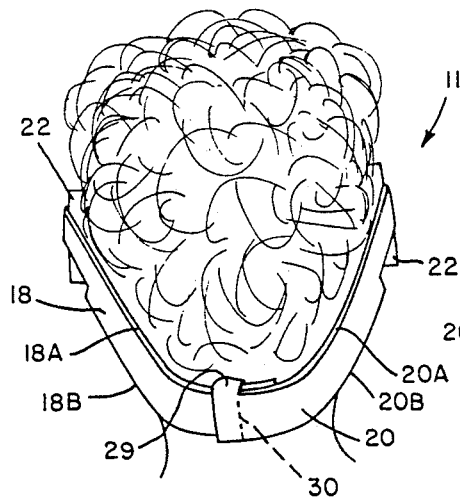
FIG. 3 is a rear view showing the protector on the wearer's head in accordance with the present invention.
Figure 4:
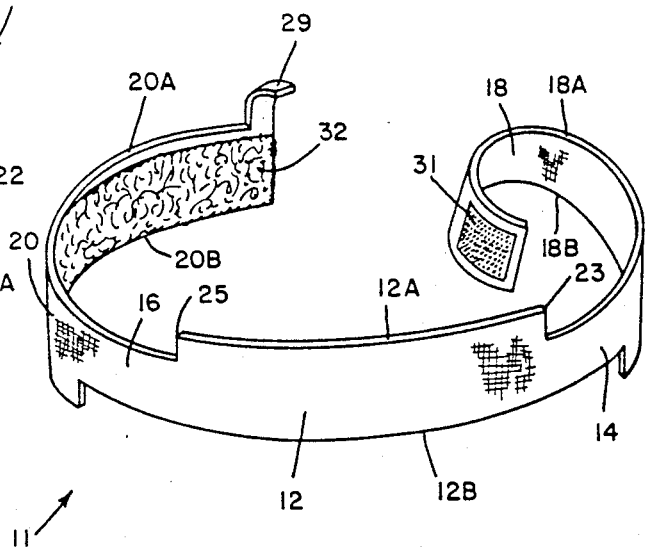
FIG. 4 is a perspective view of the protector showing the opened ends.

A preferred embodiment of the forehead, temple, ear, and neck protector 11 of the present invention when worn by a user is illustrated in FIG. 1 (front view), FIG. 2 (side view), and FIG. 3 (rear view). The protector 11 is preferably constructed of a one-piece band plus two detachable ear protectors 22 made of a flexible and extensible material, such as elasticized material made with cotton, polyester, a blend of fabrics, or various other materials capable of protecting or providing insulation to the skin. The protector 11 should be of such a shape and size as to be capable of covering and protecting the skin located directly under the entire hairline from accidental burns that can be obtained from heat based hair styling devices during the hair styling process. The protector 11 should be sufficiently designed to follow the contour of most hairlines and adjust in fit to most head sizes when applied.

A forehead protector 12 includes a band or cover portion that extends upward to meet the forehead hairline and covers the skin area from the edge of the hairline on the forehead; includes a Top Edge 12A; extends to the lower portion of the forehead, just above the eyebrows; and also includes a Bottom Edge 12B.

The forehead protector 12 of the band extends around the left side of the wearer's head to a left temple protector 14. The left temple protector 14 of the band extends vertically from the left temple protector top edge 14A to the left temple protector bottom edge 14B, for covering and protecting the left temple skin area.

The forehead protector 12 continues around the right side of the wearer's head to a right temple protector 16 of the band 11. The right temple protector 16 extends vertically from a top edge right temple protector 16A to a bottom edge right temple protector 16B, for covering and protecting the right temple skin area. As seen in FIG. 2, each temple portion has a smaller width than the width of the forehead protector.

The left temple protector 14 continues around the wearer's head to a left side neck protector 18 of the band 11. The left side neck protector 18 extends vertically from a top edge left neck protector 18A to a bottom edge left neck protector 18B, for covering and protecting the skin area of the left side of the neck.

A right temple protector 16 continues to a right side neck protector 20 of the band 11. The right side neck protector 20 extends vertically from the top edge right neck protector 20A to a bottom edge right neck protector 20B, for covering and protecting the skin area of the right side of the neck.

The present invention includes detachable ear protectors 22. The ear protectors 22 are preferably of the same structure so either may be used with the right or left ear, eliminating the need to match left and right pieces to their respective ears. This feature provides added flexibility to the wearer.

Ear protectors 22 can be made of the same flexible elastic material as the forehead protector 11 or with any material which can cover and protect the ears during the above referenced hair styling processes. As indicated by FIG. 5, the ear protector 22 is oval shaped to conveniently fit over the ears. Two single pieces of material 22 and 22A are cut into the oval shape, having a length and width a little larger than the average sized human ear. An opening 36 large enough to allow insertion of the ear is cut into the center of the oval-shaped piece 22A as indicated in FIG. 6. The two pieces are aligned and sewn together at the edges. FIG. 7 represents the ear placed inside of the ear protector. Also, the ear protectors 22 can be constructed in various ways, such as with a single piece of material. An Ear Protector Attachment Loop 35 in the form of a loop 35 can be constructed from a variety of material such as cotton or polyester. The loop 35 allows the wearer to attach the ear protectors 22 to the band at the temple protectors 14 and 16 and to slide the ear protectors along temple protectors 14 and 16 to the desired portion. Loop 35 is attached by using Velcro(TM), snaps, or similar methods of attaching the loop to the ear protector 22 as shown in FIG. 5A.

A left forehead/temple offset 23 and right forehead/temple offset 25 extend upwardly to protect the forehead, substantially follows the natural contour of most hairlines, and covers the skin where the forehead and temple hairline meet, enabling maximum coverage of the vulnerable skin area without obstructing the hair styling process and permits the band to be adapted to a wide variety of users.

A left temple protector 14 ensures the left ear protector 22 is held securely in place as shown in FIGS. 1 and 2. A right temple protector 16 ensures the right ear protector 22 is held securely in place as shown in FIGS. 1 and 2.

A fastening element 31 is attached to the outer layer of the end of the left neck protector 18. A comparable fastening element 32 is attached to the inner layer of the end of the right neck protector 20. Fastening elements 31 and 32 preferably are hook and loop type materials such as Velcro(TM), or elements can be in the form of snaps or other fasteners for securing the ends of the left and right side neck protectors 18 and 20 together so the band 11 is of a closed loop configuration to fit around the head of the wearer.

Due to the adjustability of the protective device, wearers with smaller heads will have an overlap of material at the end of the right neck protector 20. The overlapping material is held securely in place against neck protector 18 and out of the wearer's way by a tab 29, which extends outwardly relative to the longitudinal axis of protector 11, is another feature unique to this design. FIG. 3 (rear view) shows the tab in the fastened position 30. The tab 29 is held in place by the elasticity of the material used in the fabrication of the neck protectors 18 and 20 which provides a snug fit against the head of the wearer and holds the tab in place as shown in FIG. 3.

A second embodiment of a protector in accordance with the present invention is shown in FIG. 10. In this embodiment, the left side neck protector 18 is terminated on the outer layer with female snaps 33 and the right neck protector 20 is terminated on the inner layer with male snaps 34 for securing the left and right side neck protectors 18 and 20 into a closed loop configuration to fit around the head of the wearer.

OPERATION - FIGS. 1, 2, 3

The preferred embodiment for the use of the forehead, temple, ear, and neck protector 11 is clearly illustrated in FIGS. 1, 2, and 3. The wearer first places an ear protector 22 over each ear. Next, the forehead protector 12 is placed on the forehead of the wearer and the temple protectors 14 and 16 and neck protectors 18 and 20 are secured around the head directly below the hairline into a closed circular configuration. The protector is secured around the head by utilizing the chosen method for closure 31-34 as shown in FIGS. 1, 2, and 3. The protector 11 is then adjusted to a comfortable snug fit. The protector 11 should be adjusted if necessary by using a hook and loop type fastener which can be adjusted at several points to fit different size heads and to secure the ear protectors 22 and insure that the edges of the protective band meet the wearer's hairline without obstructing access to the hair being styled. Wearer's with smaller heads will have an overlap of material in the rear neck area. The overlapping material is held securely in place by stuffing the tuck 29 between the skin and the rear of the left neck protector, preventing annoyance or interruption to the user. When using ear protectors 22 with loops 35, the wearer will be required to detach the fasteners at either end of the loop 35 and reattach it over the temple protectors 14 and 16. When all adjustments have been made, the wearer will be protected from most accidental burns of the vulnerable skin area during normal use of heat based hair styling appliances.

To remove the protector 11, the wearer must first disconnect the fastened ends and then remove each individual ear protector 22.

I claim:
1. A protective device in the form of a band which covers the ears and skin located just below the entire hairline, comprising:
    (a) a band of flexible material adapted to be worn around the head of a wearer, the band comprising a forehead protector which includes an upwardly extending cover portion to meet the forehead hairline of a wearer, a temple protector portion connected with each end of the forehead protector, each temple protector portion having a smaller width than the width of the forehead protector, an ear protector portion slidably carried on each temple protector portion for sliding movement therealong, and a neck protector portion connected with each temple protector portion to simultaneously cover the skin of the wearer immediately below the hairline at the wearer's forehead, temples, ears, and neck;
    (b) adjustable connection means for joining the neck protector portions of said band of flexible material together to complete a closed loop structure around the wearer's head and to permit adjustability of the circumferential length of the device.

2. A device in accordance with claim 1 wherein said flexible material is an elasticized polyester material.

3. A device in accordance with claim 2 wherein said flexible material is an elasticized cotton material.

4. A device in accordance with claim 1 wherein the adjustable connection means includes a hook and loop fastener at each end of the band for joining the band ends to allow for adjustment to different head sizes.

5. A device in accordance with claim 4 wherein said adjustable connection means include a set of snap fasteners at each end of the band for joining the band ends to allow for adjustment to different head sizes.

6. A device in accordance with claim 1, wherein the ear protector portions are detachable from the band.

7. A device in accordance with claim 6 including releasable attaching means for attaching the detachable ear protectors to the band, the attaching means including a loop having a hook and loop fastner, the loop carried by the ear protector for releasably attaching the ear protector to the band.

8. A device in accordance with claim 1, including a means of conforming to the natural contour of most hairlines by covering the skin directly below the entire hairline.

9. A device in accordance with claim 1, wherein a single piece of material is attached vertically to the top edge of one end of an elasticized band to serve as a holder for overlap material.

10. A protective device in the form of a band which shields the ears and skin located directly below the entire hairline, comprising:
    (a) a band of flexible material which protects the skin and fits over the forehead, temples, ears, and neck, and including ear protector means slidably carried for movement along the device, a forehead protector which includes an upwardly extending forehead cover portion to meet the forehead hairline of a wearer, and a temple protector portion connected with each end of the forehead protector, each temple protector portion having a smaller width than the width of the forehead protector;
    (b) adjustable connection means for joining the end portions of said piece of flexible material together to complete a closed loop structure around the wearer's head and to permit adjustability of the circumferential length of the device to accommodate different head sizes.

11. A device in accordance with claim 10 wherein said flexible material is an elasticized polyester material.

12. A device in accordance with claim 11 wherein said flexible material is an elasticized cotton material.

13. A device in accordance with claim 10 wherein the adjustable connection means include a hook and loop fastener at each end of the band for effectively linking the band ends to allow for adjustment to different head sizes.

14. A device in accordance with claim 13 wherein said adjustable connection means includes a set of snap fasteners at the end of the band for effectively linking the band ends to allow for adjustment to different head sizes.

15. A device in accordance with claim 10 wherein the ear protector means are detachable from the device.

16. A device in accordance with claim 15 including releasable attaching means for attaching the detachable ear protector means to the band, the attaching means including a loop having a set of snap fasteners cooperable with snap fasteners on the ear protector for releasably attaching the ear protector means to the band.

17. A device in accordance with claim 10 including a means of conforming to the width and length of the skin located directly under the entire hairline of most humans.

18. A device in accordance with claim 10 wherein a strip of material is attached vertically to the top edge of one end of an elasticized band to serve as a holder for overlap material.

19. A protective device in the form of a band made of flexible material to encircle the head of a wearer, the band comprising a forehead cover portion which extends upwardly from the band to meet the forehead hairline, the forehead cover portion extends at both ends covering the skin located directly beside the left and right side temple hairline, temple cover portions that are connected to and extend from each end of the forehead cover portion, each temple cover portion having a smaller width than the width of the forehead cover portion, ear protectors slidably carried by the temple cover portions to cover the left and right ears of a wearer, wherein the temple portions have a length sufficient to permit their free ends to be joined together around the neck at different intersecting points to accommodate different sized heads, while covering the skin located directly under the neck hairline.

* * * * *